United States Patent
Baileykobayashi et al.

(10) Patent No.: US 11,780,903 B2
(45) Date of Patent: Oct. 10, 2023

(54) PEPTIDE SUPPRESSING BINDING OF CTLA4 TO B7 PROTEINS, AND USE THEREOF

(71) Applicant: TOAGOSEI CO., LTD., Tokyo (JP)

(72) Inventors: Nahoko Baileykobayashi, Tsukuba (JP); Tetsuhiko Yoshida, Tsukuba (JP)

(73) Assignee: TOAGOSEI CO., LTD., Tokyo (JP)

( * ) Notice: Subject to any disclaimer, the term of this patent is extended or adjusted under 35 U.S.C. 154(b) by 191 days.

(21) Appl. No.: 17/116,244

(22) Filed: Dec. 9, 2020

(65) Prior Publication Data

US 2021/0238251 A1 Aug. 5, 2021

(30) Foreign Application Priority Data

Jan. 30, 2020 (JP) ................. 2020-013463

(51) Int. Cl.
*C07K 14/705* (2006.01)
*A61K 38/00* (2006.01)

(52) U.S. Cl.
CPC .. *C07K 14/70503* (2013.01); *C07K 14/70521* (2013.01); *A61K 38/00* (2013.01); *C07K 2319/02* (2013.01); *C07K 2319/30* (2013.01)

(58) Field of Classification Search
CPC combination set(s) only.
See application file for complete search history.

(56) References Cited

U.S. PATENT DOCUMENTS

2019/0233513 A1* 8/2019 Cao et al. ............. C07K 16/28

FOREIGN PATENT DOCUMENTS

WO 2000032231 A1 6/2000

OTHER PUBLICATIONS

Acevedo et al. LIM Kinase 2 is Widely Expressed in All Tissues, 2006, The Journal of Histochemistry & Cytochemistry, vol. 54(5), pp. 487-501 (Year: 2006).*
Kovjazin et al., Signal Peptides and Trans-Membrane Regions are Broadly Immunogenic and Have High CD8+ T Cell Epitope Densities: Implications for Vaccine Development, 2011, Molecular Immunology, vol. 48, pp. 1009-1018 (Year: 2011).*
Owji et al., A Comprehensive Review of Signal Peptides: Structure, Roles, and Applications, 2018, European Journal of Cell Biology, vol. 97, pp. 422-441 (Year: 2018).*
Ramanayake Mudiyanselage et al., An Immune-Stimulatory Helix-Loop-Helix Peptide: Selective Inhibition of CTLA-4-B7 Interaction, 2019, ACS Chemical Biology, vol. 15, pp. 360-368 (Year: 2019).*
Ott, Patrick A. et al. "CTLA-4 and PD-1/PD-L1 Blockade: New Immunotherapeutic Modalities with Durable Clinical Benefit in Melanoma Patients." Clinical Cancer Research, vol. 19, No. 19, 2013, pp. 5300-5309.

* cited by examiner

*Primary Examiner* — Daniel E Kolker
*Assistant Examiner* — Danaya L Middleton
(74) *Attorney, Agent, or Firm* — Occhiuti & Rohlicek LLP (57) ABSTRACT

The synthetic peptide disclosed herein is a synthetic peptide which is artificially synthesized for suppressing binding of CTLA4 to at least one of B7 proteins B7-1 and B7-2. The synthetic peptide includes a CTLA4-B7 protein binding inhibitory peptide sequence. The CTLA4-B7 protein binding inhibitory peptide sequence is any one of amino acid sequences shown in the following (1) to (3): (1) a TIM3-SP-related sequence; (2) an LAGS-SP-related sequence; and (3) a CTLA4-SP-related sequence. Here, the total number of amino acid residues in the above-described synthetic peptide is 100 or less.

3 Claims, 1 Drawing Sheet

Specification includes a Sequence Listing.

FIG.1

FIG.2

SEQUENCE LISTING

```
<160> NUMBER OF SEQ ID NOS: 39

<210> SEQ ID NO 1
<211> LENGTH: 21
<212> TYPE: PRT
<213> ORGANISM: Homo sapiens

<400> SEQUENCE: 1

Met Phe Ser His Leu Pro Phe Asp Cys Val Leu Leu Leu Leu Leu
1               5                   10                  15

Leu Leu Thr Arg Ser
            20

<210> SEQ ID NO 2
<211> LENGTH: 19
<212> TYPE: PRT
<213> ORGANISM: Mus musculus

<400> SEQUENCE: 2

Met Phe Ser Gly Leu Thr Leu Asn Cys Val Leu Leu Leu Leu Gln Leu
1               5                   10                  15

Leu Leu Ala

<210> SEQ ID NO 3
<211> LENGTH: 21
<212> TYPE: PRT
<213> ORGANISM: Rattus norvegicus

<400> SEQUENCE: 3

Met Phe Ser Trp Leu Pro Phe Ser Cys Ala Leu Leu Leu Leu Gln Pro
1               5                   10                  15

Leu Pro Ala Arg Ser
            20

<210> SEQ ID NO 4
<211> LENGTH: 22
<212> TYPE: PRT
<213> ORGANISM: Homo sapiens

<400> SEQUENCE: 4

Met Trp Glu Ala Gln Phe Leu Gly Leu Leu Phe Leu Gln Pro Leu Trp
1               5                   10                  15

Val Ala Pro Val Lys Pro
            20

<210> SEQ ID NO 5
<211> LENGTH: 28
<212> TYPE: PRT
<213> ORGANISM: Homo sapiens

<400> SEQUENCE: 5

Met Trp Glu Ala Gln Phe Leu Gly Leu Leu Phe Leu Gln Pro Leu Trp
1               5                   10                  15
```

Val Ala Pro Val Lys Pro Leu Gln Pro Gly Ala Glu
            20                  25

<210> SEQ ID NO 6
<211> LENGTH: 23
<212> TYPE: PRT
<213> ORGANISM: Mus musculus

<400> SEQUENCE: 6

Met Arg Glu Asp Leu Leu Leu Gly Phe Leu Leu Gly Leu Leu Trp
1               5                   10                  15

Glu Ala Pro Val Val Ser Ser
            20

<210> SEQ ID NO 7
<211> LENGTH: 23
<212> TYPE: PRT
<213> ORGANISM: Rattus norvegicus

<400> SEQUENCE: 7

Met Arg Gln Asp Leu Phe Leu Asp Leu Leu Leu Gln Leu Leu Trp
1               5                   10                  15

Glu Ala Pro Val Val Ser Ser
            20

<210> SEQ ID NO 8
<211> LENGTH: 35
<212> TYPE: PRT
<213> ORGANISM: Homo sapiens

<400> SEQUENCE: 8

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys
        35

<210> SEQ ID NO 9
<211> LENGTH: 35
<212> TYPE: PRT
<213> ORGANISM: Canis familiaris

<400> SEQUENCE: 9

Met Ala Gly Phe Gly Phe Arg Arg His Gly Val Gln Pro Asp Leu Ala
1               5                   10                  15

Ser Arg Thr Trp Pro Cys Thr Ala Leu Phe Ser Leu Leu Phe Ile Pro
            20                  25                  30

Val Phe Ser
        35

<210> SEQ ID NO 10
<211> LENGTH: 35
<212> TYPE: PRT
<213> ORGANISM: Mus musculus

<400> SEQUENCE: 10

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

```
<210> SEQ ID NO 11
<211> LENGTH: 35
<212> TYPE: PRT
<213> ORGANISM: Oryctolagus cuniculus

<400> SEQUENCE: 11

Met Ala Arg Leu Gly Phe Gln Arg Gln Gly Thr Gln Leu Asp Leu Ala
1               5                   10                  15
Ser Arg Thr Trp Ser Cys Ala Ala Leu Phe Ser Leu Leu Phe Leu Pro
            20                  25                  30
Val Phe Ser
        35

<210> SEQ ID NO 12
<211> LENGTH: 35
<212> TYPE: PRT
<213> ORGANISM: Sus scrofa

<400> SEQUENCE: 12

Met Ala Cys Ser Gly Phe Gln Ser His Gly Ala Trp Leu Glu Leu Thr
1               5                   10                  15
Ser Arg Thr Trp Pro Cys Thr Ala Leu Phe Ser Leu Leu Phe Ile Pro
            20                  25                  30
Val Phe Ser
        35

<210> SEQ ID NO 13
<211> LENGTH: 37
<212> TYPE: PRT
<213> ORGANISM: Aotus trivirgatus

<400> SEQUENCE: 13

Met Ala Cys Leu Gly Phe Gln Arg His Lys Ala Gln Leu Asp Leu Ala
1               5                   10                  15
Thr Arg Thr Trp Pro Cys Thr Phe Leu Phe Ser Leu Leu Phe Ile Leu
            20                  25                  30
Val Phe Ser Asn Ala
        35

<210> SEQ ID NO 14
<211> LENGTH: 37
<212> TYPE: PRT
<213> ORGANISM: Papio anubis

<400> SEQUENCE: 14

Met Ala Cys Leu Gly Phe Gln Arg His Lys Ala Gln Leu Asn Leu Ala
1               5                   10                  15
Thr Arg Thr Arg Pro Tyr Thr Leu Leu Phe Ser Leu Leu Phe Ile Pro
            20                  25                  30
Val Phe Ser Lys Ala
        35

<210> SEQ ID NO 15
<211> LENGTH: 37
<212> TYPE: PRT
<213> ORGANISM: Macaca mulatta

<400> SEQUENCE: 15
```

```
Met Ala Cys Leu Gly Phe Gln Arg His Lys Ala Arg Leu Asn Leu Ala
1               5                   10                  15

Thr Arg Thr Arg Pro Tyr Thr Leu Leu Phe Ser Leu Leu Phe Ile Pro
            20                  25                  30

Val Phe Ser Lys Ala
        35

<210> SEQ ID NO 16
<211> LENGTH: 14
<212> TYPE: PRT
<213> ORGANISM: Artificial Sequence
<220> FEATURE:
<223> OTHER INFORMATION: synthetic peptide

<400> SEQUENCE: 16

Arg Ser Arg Lys Tyr Thr Ser Trp Tyr Val Ala Leu Lys Arg
1               5                   10

<210> SEQ ID NO 17
<211> LENGTH: 19
<212> TYPE: PRT
<213> ORGANISM: Artificial Sequence
<220> FEATURE:
<223> OTHER INFORMATION: synthetic peptide

<400> SEQUENCE: 17

Met Ala Lys Ser Ile Arg Ser Lys His Arg Arg Gln Met Arg Met Met
1               5                   10                  15

Lys Arg Glu

<210> SEQ ID NO 18
<211> LENGTH: 16
<212> TYPE: PRT
<213> ORGANISM: Artificial Sequence
<220> FEATURE:
<223> OTHER INFORMATION: synthetic peptide

<400> SEQUENCE: 18

Met Ala Arg Arg Arg Arg His Arg Gly Pro Arg Arg Pro Arg Pro Pro
1               5                   10                  15

<210> SEQ ID NO 19
<211> LENGTH: 19
<212> TYPE: PRT
<213> ORGANISM: Artificial Sequence
<220> FEATURE:
<223> OTHER INFORMATION: synthetic peptide

<400> SEQUENCE: 19

Gly Arg Cys Arg Arg Leu Ala Asn Phe Gly Pro Arg Lys Arg Arg Arg
1               5                   10                  15

Arg Arg Arg

<210> SEQ ID NO 20
<211> LENGTH: 16
<212> TYPE: PRT
<213> ORGANISM: Artificial Sequence
<220> FEATURE:
<223> OTHER INFORMATION: synthetic peptide

<400> SEQUENCE: 20

Arg Arg Arg Lys Arg Asn Arg Asp Ala Arg Arg Arg Arg Arg Lys Gln
1               5                   10                  15
```

-continued

```
<210> SEQ ID NO 21
<211> LENGTH: 17
<212> TYPE: PRT
<213> ORGANISM: Artificial Sequence
<220> FEATURE:
<223> OTHER INFORMATION: synthetic peptide

<400> SEQUENCE: 21

Met Gln Arg Lys Pro Thr Ile Arg Arg Lys Asn Leu Arg Leu Arg Arg
1               5                   10                  15

Lys

<210> SEQ ID NO 22
<211> LENGTH: 7
<212> TYPE: PRT
<213> ORGANISM: Artificial Sequence
<220> FEATURE:
<223> OTHER INFORMATION: synthetic peptide

<400> SEQUENCE: 22

Ile Met Arg Arg Arg Gly Leu
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic peptide

<400> SEQUENCE: 23

Lys Lys Leu Lys Lys Arg Asn Lys
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic peptide

<400> SEQUENCE: 24

Arg Arg Arg Ala Asn Asn Arg Arg Arg
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic peptide

<400> SEQUENCE: 25

Arg Lys Lys Arg Lys Lys Lys
1               5

<210> SEQ ID NO 26
<211> LENGTH: 15
<212> TYPE: PRT
<213> ORGANISM: Artificial Sequence
<220> FEATURE:
<223> OTHER INFORMATION: synthetic peptide

<400> SEQUENCE: 26

Lys Arg Lys Gly Lys Leu Lys Asn Lys Gly Ser Lys Arg Lys Lys
1               5                   10                  15
```

```
<210> SEQ ID NO 27
<211> LENGTH: 18
<212> TYPE: PRT
<213> ORGANISM: Artificial Sequence
<220> FEATURE:
<223> OTHER INFORMATION: synthetic peptide

<400> SEQUENCE: 27

Ser Lys Arg Leu Ser Ser Arg Ala Arg Lys Arg Ala Ala Lys Arg Arg
1               5                   10                  15

Leu Gly

<210> SEQ ID NO 28
<211> LENGTH: 14
<212> TYPE: PRT
<213> ORGANISM: Artificial Sequence
<220> FEATURE:
<223> OTHER INFORMATION: synthetic peptide

<400> SEQUENCE: 28

Lys Arg Pro Arg Arg Pro Ser Arg Pro Phe Arg Lys Pro
1               5                   10

<210> SEQ ID NO 29
<211> LENGTH: 13
<212> TYPE: PRT
<213> ORGANISM: Artificial Sequence
<220> FEATURE:
<223> OTHER INFORMATION: synthetic peptide

<400> SEQUENCE: 29

Lys Lys Arg Thr Leu Arg Lys Asn Asp Arg Lys Lys Arg
1               5                   10

<210> SEQ ID NO 30
<211> LENGTH: 8
<212> TYPE: PRT
<213> ORGANISM: Artificial Sequence
<220> FEATURE:
<223> OTHER INFORMATION: synthetic peptide

<400> SEQUENCE: 30

Trp Arg Arg Gln Ala Arg Phe Lys
1               5

<210> SEQ ID NO 31
<211> LENGTH: 9
<212> TYPE: PRT
<213> ORGANISM: Artificial Sequence
<220> FEATURE:
<223> OTHER INFORMATION: synthetic peptide

<400> SEQUENCE: 31

Arg Lys Lys Arg Arg Gln Arg Arg Arg
1               5

<210> SEQ ID NO 32
<211> LENGTH: 11
<212> TYPE: PRT
<213> ORGANISM: Artificial Sequence
<220> FEATURE:
<223> OTHER INFORMATION: synthetic peptide

<400> SEQUENCE: 32

Tyr Ala Arg Ala Ala Ala Arg Gln Ala Arg Ala
```

-continued

<210> SEQ ID NO 33
<211> LENGTH: 18
<212> TYPE: PRT
<213> ORGANISM: Artificial Sequence
<220> FEATURE:
<223> OTHER INFORMATION: synthetic peptide

<400> SEQUENCE: 33

Lys Gly Arg Gln Val Lys Val Trp Phe Gln Asn Arg Arg Met Lys Trp
1               5                   10                  15

Lys Lys

<210> SEQ ID NO 34
<211> LENGTH: 48
<212> TYPE: PRT
<213> ORGANISM: Artificial Sequence
<220> FEATURE:
<223> OTHER INFORMATION: synthetic peptide

<400> SEQUENCE: 34

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Lys Arg Thr Leu Arg Lys Asn Asp Arg Lys Lys Arg
                35                  40                  45

<210> SEQ ID NO 35
<211> LENGTH: 34
<212> TYPE: PRT
<213> ORGANISM: Artificial Sequence
<220> FEATURE:
<223> OTHER INFORMATION: synthetic peptide

<400> SEQUENCE: 35

Met Phe Ser His Leu Pro Phe Asp Cys Val Leu Leu Leu Leu Leu Leu
1               5                   10                  15

Leu Leu Thr Arg Ser Lys Lys Arg Thr Leu Arg Lys Asn Asp Arg Lys
                20                  25                  30

Lys Arg

<210> SEQ ID NO 36
<211> LENGTH: 41
<212> TYPE: PRT
<213> ORGANISM: Artificial Sequence
<220> FEATURE:
<223> OTHER INFORMATION: synthetic peptide

<400> SEQUENCE: 36

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Lys Lys Arg Thr
                20                  25                  30

Leu Arg Lys Asn Asp Arg Lys Lys Arg
            35                  40

<210> SEQ ID NO 37
<211> LENGTH: 20
<212> TYPE: PRT
<213> ORGANISM: Artificial Sequence
<220> FEATURE:

```
<223> OTHER INFORMATION: synthetic peptide

<400> SEQUENCE: 37

Met Gln Ile Pro Gln Ala Pro Trp Pro Val Val Trp Ala Val Leu Gln
1               5                   10                  15

Leu Gly Trp Arg
            20

<210> SEQ ID NO 38
<211> LENGTH: 40
<212> TYPE: PRT
<213> ORGANISM: Artificial Sequence
<220> FEATURE:
<223> OTHER INFORMATION: synthetic peptide

<400> SEQUENCE: 38

Met Gln Ile Pro Gln Ala Pro Trp Pro Val Val Trp Ala Val Leu Gln
1               5                   10                  15

Leu Gly Trp Arg Met Gln Ile Pro Gln Ala Pro Trp Pro Val Val Trp
            20                  25                  30

Ala Val Leu Gln Leu Gly Trp Arg
        35                  40

<210> SEQ ID NO 39
<211> LENGTH: 13
<212> TYPE: PRT
<213> ORGANISM: Artificial Sequence
<220> FEATURE:
<223> OTHER INFORMATION: synthetic peptide

<400> SEQUENCE: 39

Lys Lys Arg Thr Leu Arg Lys Asn Asp Arg Lys Lys Arg
1               5                   10
```

PEPTIDE SUPPRESSING BINDING OF CTLA4 TO B7 PROTEINS, AND USE THEREOF

CROSS-REFERENCE TO RELATED APPLICATIONS

This application claims the benefit of foreign priority to Japanese Patent Application No. 2020-013463, filed on Jan. 30, 2020, the entire contents of which are incorporated herein by reference.

TECHNICAL FIELD

The present invention relates to a peptide suppressing binding of CTLA4 to B7 proteins, and use thereof. Specifically, the present invention relates to a synthetic peptide having an amino acid sequence having a structure that suppresses binding of CTLA4 to at least one of B7-1 and B7-2, and use thereof.

TECHNICAL BACKGROUND

In recent years, so-called "immunotherapy" which utilizes a function of an immune monitoring mechanism of a living body has been attracting attention as a treatment method for cancer. Basic research and clinical research on "immunotherapy" are being actively conducted. An immune monitoring mechanism can recognize and remove cancerous cells (cancer cells and tumor cells) as foreign substances. Growth of cancer cells and expansion of tumor tissue can be suppressed and prevented by the function of such an immune monitoring mechanism. Various immune cells are involved in elimination of the immune monitoring mechanism. Among these, T cells can mainly conduct elimination of tumor cells and inhibition of expansion of tumor tissue. T cells have become a main target of various present studies on cancer immunotherapy.

Incidentally, activation of T cells is controlled by signals via, for example, a T cell receptor (TCR) and a co-stimulatory receptor. For example, when antigen-presenting cells (such as dendritic cells) presenting tumor antigens transmit information on the tumor antigens to T cells via a TCR, B7 proteins (for example, CD80 for B7-1 and CD86 for B7-2) on the antigen-presenting cells bind to CD28 which is one of the co-stimulatory receptors on the T cells. Then, activation signals are transmitted to the T cells.

On the other hand, T cells express cytotoxic T lymphocyte antigen 4 (CTLA4) as another co-stimulatory receptor. CTLA4 can bind to B7-1 and B7-2. Since CTLA4 has an inhibitory motif as an intracellular domain, the above-described binding generates inhibitory signals for the T cells. In a case where the activation of the T cells is suppressed by the binding of CTLA4 to B7-1 and B7-2, growth of cytotoxic T cells is suppressed. This can inhibit elimination of tumor cells. This can be a factor that promotes expansion of tumor tissue.

Incidentally, CTLA4 has become an important target in present cancer immunotherapy. In WO 2000/032231, it has been confirmed that administration of anti-CTLA4 antibodies suppresses growth of some tumors. Moreover, the anti-CTLA4 antibodies are used as therapeutic agents in clinical practice (WO 2000/032231, CTLA-4 and PD-1/PD-L1 Blockade: New Immunotherapeutic Modalities with Durable Clinical Benefit in Melanoma Patients, 2013, Clinical Cancer Research, 19, 5300-5309 (Ott, et al.))

However, anti-CTLA4 antibodies as therapeutic agents are extremely expensive. For this reason, for example, the cost for cancer medical treatment has become a serious problem, due to treatment with the therapeutic agents.

The present invention is created to provide relatively inexpensive peptide pharmaceuticals that can avoid suppression of activation of T cells and suppression of growth of cytotoxic T cells through technology capable of suppressing binding of CTLA4 to at least one of B7-1 and B7-2, that is, through inhibiting binding of CTLA4 expressed on surfaces of T cells to B7 proteins without using expensive antibodies.

SUMMARY OF THE INVENTION

The present inventor has focused on membrane proteins of T cells capable of suppressing functions of T cells. Surprisingly, the present inventor has found that synthetic peptides having amino acid sequences constituting signal peptides of CTLA4, TIM3, and LAGS which are membrane proteins as described above inhibit binding of CTLA4 to at least one of B7-1 and B7-2, and has completed the present invention.

That is, a synthetic peptide disclosed herein is a synthetic peptide which is artificially synthesized and suppresses binding of cytotoxic T lymphocyte antigen 4 (CTLA4) to at least one of B7 proteins B7-1 and B7-2 (hereinafter, also simply referred to as "B7 proteins" in the present specification). The peptide includes a CTLA4-B7 protein binding inhibitory peptide sequence which suppresses binding of CTLA4 to B7 proteins.

The CTLA4-B7 protein binding inhibitory peptide sequence is any one of amino acid sequences shown in the following (1) to (3):

(1) a TIM3-SP-related sequence consisting of an amino acid sequence constituting a signal peptide (SP) of T-cell immunoglobulin and mucin domain 3 (TIM3), or a modified amino acid sequence in which one, two, or three amino acid residues in the amino acid sequence are deleted, substituted, or added;

(2) an LAGS-SP-related sequence consisting of an amino acid sequence constituting a signal peptide of lymphocyte activation gene-3 (LAGS), or a modified amino acid sequence in which one, two, or three amino acid residues in the amino acid sequence are deleted, substituted, or added; and (3) a CTLA4-SP-related sequence consisting of an amino acid sequence constituting a signal peptide of CTLA4, or a modified amino acid sequence in which one, two, or three amino acid residues in the amino acid sequence are deleted, substituted, or added.

In a preferred aspect, the total number of amino acid residues in the synthetic peptide disclosed herein is 100 or less. It is more preferable that the total number of amino acid residues be 80 or less (for example, 70 or less, 60 or less, 50 or less, or 40 or less) from the viewpoints of production cost, ease of synthesis, and handling properties.

In a preferred aspect, the above-described CTLA4-B7 protein binding inhibitory peptide sequence of the synthetic peptide disclosed herein is an amino acid sequence shown in any one of SEQ ID NOs: 1 to 15.

In a preferred aspect, the synthetic peptide disclosed herein has an amino acid sequence shown in any one of SEQ ID NOs: 34 to 36.

In addition, the present invention provides a composition including: any of the synthetic peptides (CTLA4-B7 protein binding inhibitory peptides) disclosed herein; and at least one pharmaceutically acceptable carrier, in which binding of CTLA4 to B7 proteins is suppressed.

Such a composition contains the synthetic peptide disclosed herein, and therefore, can be utilized as a CTLA4-B7 protein binding inhibitory agent.

In addition, the present invention provides a method for suppressing binding of CTLA4 to at least one of B7 proteins B7-1 and B7-2, in vitro or in vivo.

This method includes supplying the above-described synthetic peptide at least once to a system in which CTLA4, and B7-1 or B7-2 coexist.

In the method with such a configuration, the synthetic peptide disclosed herein can be supplied to suppress binding of CTLA4 to the B7 proteins.

BRIEF DESCRIPTION OF THE DRAWINGS

FIG. 1 is a graph showing results of tests of binding CTLA4 to B7-1 in Test Example 2, and FIG. 2 is a graph showing results of tests of binding CTLA4 to B7-2 in Test Example 3.

DESCRIPTION OF THE RELATED EMBODIMENTS

Hereinafter, a preferred embodiment of the present invention will be described. Matters (for example, general matters like matters relating to chemical synthesis methods of peptides, cell culture techniques, and preparation of compositions containing peptides as components) other than those (for example, a primary structure or a chain length of a synthetic peptide disclosed herein) specifically mentioned in the present specification and necessary for the practice of the present invention can be recognized by those skilled in the art as design matters based on techniques in the related art in the fields such as cell engineering, physiology, medicine, pharmacy, organic chemistry, biochemistry, genetic engineering, protein engineering, molecular biology, and genetics. The present invention can be implemented based on the contents disclosed in the present specification and common technical knowledge in the field. In the following description, amino acids are represented by a single-character notation (but by a three-character notation in a sequence listing).

Entire contents of all references cited in the present specification are incorporated in the present specification by reference.

In addition, the "synthetic peptide" in the present specification refers to peptide fragments of which peptide chains do not exist independently and stably in nature and which are artificially produced through chemical synthesis or biosynthesis (that is, production based on genetic engineering) and can stably exist in a predetermined composition. Here, the "peptide" is a term referring to an amino acid polymer having a plurality of peptide bonds and is not limited by the number of amino acid residues contained in peptide chains. However, the "peptide" referred to herein typically has a relatively small molecular weight as the total number of amino acid residues is approximately 100 or less.

In addition, unless otherwise specified, the "amino acid residues" in the present specification is a term including an N-terminal amino acid and a C-terminal amino acid of a peptide chain.

In the amino acid sequences described in the present specification, the N-terminus is always on the left side and the C-terminus is always on the right side.

The "modified amino acid sequence" with respect to a predetermined amino acid sequence in the present specification refers to an amino acid sequence in which one to some number (typically 9 or less, preferably 5 or less) of amino acid residues, for example, one, two, or three amino acid residues are deleted, substituted, or added (inserted) without impairing the function (that is, properties of suppressing binding of CTLA4 to B7 proteins) of the predetermined amino acid sequence.

For example, a sequence (for example, a sequence in which a basic amino acid residue is substituted with another basic amino acid residue: for example, a mutual substitution between a lysine residue and an arginine residue) resulting from so-called a conservative substitution (conservative amino acid replacement) in which one, two or three amino acid residues are conservatively substituted or a sequence in which one, two, or three amino acid residues in a predetermined amino acid sequence are added (inserted) or deleted is a typical example included in the modified amino acid sequence referred to in the present specification.

Accordingly, the synthetic peptides disclosed herein as examples include a synthetic peptide having an amino acid sequence that is a modified amino acid sequence in which one, two, or three amino acid residues in an amino acid sequence of each sequence number is substituted (for example, conservatively substituted as described above), deleted, or added and which similarly shows CTLA4-B7 protein binding inhibitory properties in addition to a synthetic peptide consisting of the same amino acid sequence as that of each sequence number.

The artificially synthesized synthetic peptide disclosed herein is a peptide with a short chain which has been found to suppress binding with B7 proteins (that is, CTLA4-B7 protein binding inhibitory properties) and does not exist in nature, and is a peptide including any one of amino acid sequences shown in (1) to (3) below.

(1) TIM3-SP-related sequence (2) LAGS-SP-related sequence, and (3) CTLA4-SP-related sequence Here, the TIM3-SP-related sequence refers to an amino acid sequence constituting a signal peptide (SP) of a protein constituting T-cell immunoglobulin and mucin domain 3 (TIM3), or a modified amino acid sequence thereof.

TIM3 is typically a membrane protein (UniProtKB-Q8TDQ0) consisting of about 301 amino acid residues. Ott et al. discloses that TIM3 is expressed on surfaces of T cells and can suppress the function of T cells.

In addition, the LAG3-SP-related sequence refers to an amino acid sequence constituting SP of a protein constituting lymphocyte activation gene 3 (LAG3), or a modified amino acid sequence thereof.

LAG3 is typically a membrane protein (UniProtKB-P18627) consisting of about 525 amino acid residues. Ott et al. discloses that LAG3 is expressed on surfaces of T cells and can suppress the function of T cells.

The CTLA4-SP-related sequence refers to an amino acid sequence constituting SP of a protein constituting cytotoxic T lymphocyte antigen 4 (CTLA4), or a modified amino acid sequence thereof.

CTLA4 is typically a membrane protein (UniProtKB-P16410) consisting of about 223 amino acid residues. WO 2000/032231 and Ott et al. disclose that CTLA4 is expressed on surfaces of T cells and functions as, for example, a negative regulator that suppresses excessive activation of T cells through binding with CD80 and CD86 (B7-1 and B7-2) expressed on surfaces of antigen-presenting cells (for example, dendritic cells).

However, it has not been found that signal peptides of TIM3, LAG3, and CTLA4 themselves have CTLA4-B7 protein binding inhibitory properties, and it was completely unexpected at the time of filing the present application that amino acid sequences of such signal peptides could be synthesized to obtain an artificially synthesized CTLA4-B7 protein binding inhibitory peptide.

For example, information on genes (including a case of cDNA) which encode TIM3, LAG3, and CTLA4 and amino acid sequence information can be acquired by accessing knowledge bases (databases) of various public international organizations. For example, all amino acid sequence information on TIM3, LAG3, and CTLA4 derived from various species and amino acid sequence information on signal peptides can be obtained in Universal Protein Resource (UniProt). According to the database, at least information on TIM3, LAG3, and CTLA4 in mammals such as humans, dogs, mice, rats, rabbits, and pigs can be acquired.

TIM3-SP-related sequences according to (1) described above which are preferably used in carrying out the present invention are respectively shown in, for example, SEQ ID NOs: 1 to 3.

Specifically, an amino acid sequence of SEQ ID NO: 1 is an amino acid sequence consisting of 21 amino acid residues in total constituting a signal peptide of TIM3 derived from a human (*Homo sapiens*).

Although the amino acid sequence constituting the signal peptide of human-derived TIM3 is shown in the above-described SEQ ID NO: 1, the sequence is merely an example, and available amino acid sequences are not limited thereto.

For example, an amino acid sequence of SEQ ID NO: 2 is an amino acid sequence consisting of 19 amino acid residues in total constituting a signal peptide of TIM3 (UniProtKB-Q8VIMO) derived from a mouse (*Mus musculus*).

For example, an amino acid sequence of SEQ ID NO: 3 is an amino acid sequence consisting of 21 amino acid residues in total constituting a signal peptide of TIM3 (UniProtKB-P0C0K5) derived from a rat (*Rattus norvegicus*).

LAG3-SP-related sequences according to (2) described above which are preferably used in carrying out the present invention are respectively shown in, for example, SEQ ID NOs: 4 to 7.

Specifically, an amino acid sequence of SEQ ID NO: 4 is an amino acid sequence consisting of 22 amino acid residues in total constituting a signal peptide of LAG3 derived from a human (*Homo sapiens*).

Although the amino acid sequence constituting the signal peptide of human-derived LAG3 is shown in the above-described SEQ ID NO: 4, the sequence is merely an example, and available amino acid sequences are not limited thereto.

For example, an amino acid sequence shown in SEQ ID NO: 5 may be used as the LAG3-SP-related sequence according to (2) described above. The amino acid sequence of SEQ ID NO: 5 is an amino acid sequence in which 6 amino acid residues are bound to the N-terminus of the above-described amino acid sequence of SEQ ID NO: 4.

In addition, for example, the amino acid sequence of SEQ ID NO: 6 is an amino acid sequence consisting of 23 amino acid residues in total constituting a signal peptide of LAG3 (UniProtKB-Q61790) derived from a mouse (*Mus musculus*).

For example, an amino acid sequence of SEQ ID NO: 7 is an amino acid sequence consisting of 23 amino acid residues in total constituting a signal peptide of LAG3 (UniProtKB-Q5BK54) derived from a rat (*Rattus norvegicus*).

CTLA4-SP-related sequences according to (3) described above which are preferably used in carrying out the present invention are respectively shown in, for example, SEQ ID NOs: 8 to 15.

Specifically, an amino acid sequence of SEQ ID NO: 8 is an amino acid sequence consisting of 35 amino acid residues in total constituting a signal peptide of CTLA4 derived from a human (*Homo sapiens*).

Although the amino acid sequence constituting the signal peptide of human-derived CTLA4 is shown in the above-described SEQ ID NO: 8, the sequence is merely an example, and available amino acid sequences are not limited thereto.

For example, an amino acid sequence of SEQ ID NO: 9 is an amino acid sequence consisting of 35 amino acid residues in total constituting a signal peptide of CTLA4 (UniProtKB-Q9XSI1) derived from a dog (*Canis familiaris*).

In addition, the amino acid sequence of SEQ ID NO: 10 is an amino acid sequence consisting of 35 amino acid residues in total constituting a signal peptide of CTLA4 (UniProtKB-P09793) derived from a mouse (*Mus musculus*).

Furthermore, the amino acid sequence of SEQ ID NO: 11 is an amino acid sequence consisting of 35 amino acid residues in total constituting a signal peptide of CTLA4 (UniProtKB-42072) derived from a rabbit (Oryctilagus *cuniculus*).

In addition, the amino acid sequence of SEQ ID NO: 12 is an amino acid sequence consisting of 35 amino acid residues in total constituting a signal peptide of CTLA4 (UniProtKB-Q9MYX7) derived from a pig (*Sus scrofa*).

Information on genes (including a case of cDNA) which encode CTLA4 and amino acid sequence information can be acquired from the National Center for Biotechnology Information (NCBI).

For example, an amino acid sequence of SEQ ID NO: 13 is an amino acid sequence consisting of 37 amino acid residues in total constituting a signal peptide of CTLA4 (GenBank: AAK37530.1) derived from a night monkey (*Aotus trivirgatus*).

In addition, an amino acid sequence of SEQ ID NO: 14 is an amino acid sequence consisting of 37 amino acid residues in total constituting a signal peptide of CTLA4 (NP_001106104.1) derived from an anubis baboon (*Papio anubis*).

Furthermore, an amino acid sequence of SEQ ID NO: 15 is an amino acid sequence consisting of 37 amino acid residues in total constituting a signal peptide of CTLA4 (NP_001038204.1) derived from a rhesus macaque (*Macaca* mulatta).

All of the above-described amino acid sequences shown in SEQ ID NOs: 8 to 15 can be preferably employed as CTLA4-SP-related sequences.

The synthetic peptide disclosed herein may contain a sequence (amino acid residue) part other than the above-described CTLA4-B7 protein binding inhibitory peptide sequences as long as the CTLA4-B7 protein binding inhibitory properties are not lost. The other sequence portion may be an auxiliary peptide sequence capable of more effectively realizing the function (that is, CTLA4-B7 protein binding inhibitory properties) of a CTLA4-B7 protein binding inhibitory peptide sequence, for example.

For example, the auxiliary peptide sequence may be added to a CTLA4-B7 protein binding inhibitory peptide sequence to improve solubility or dispersibility of a synthetic peptide with respect to a predetermined solvent.

The above-described predetermined solvent is not particularly limited, but examples thereof include buffer solutions such as water, physiological saline, and a phosphate buffer solution (PBS), a cell culture solution, organic solvents such as an aqueous alcohol (such as ethanol) solution, dimethyl sulfoxide (DMSO), and lower alcohols such as methanol and ethanol. The amino acid sequence of the auxiliary peptide sequence can be appropriately determined depending on a solvent in which a synthetic peptide is to be dissolved or dispersed. The auxiliary peptide sequence may contain, for example, a plurality of hydrophilic amino acid residues (typically, for example, 20 or less, 10 or less, and 5 or less), or may contain, for example, a plurality of hydrophobic amino acid residues (typically, for example, 20 or less, 10 or less, and 5 or less). In addition, an auxiliary peptide sequence may be designed by combining a hydrophilic amino acid residue and a hydrophobic amino acid residue to preferably set the solubility or dispersibility in the above-described predetermined solvent.

Examples of hydrophilic amino acids include polar amino acids (for example, polar uncharged amino acids, acidic amino acids, and basic amino acids). Examples of hydrophobic amino acids include non-polar amino acids.

The auxiliary amino acid sequence may be, for example, an amino acid sequence (that is, a CPP-related sequence) which functions as a cell penetrating peptide (CPP).

Examples of the CPP-related sequence include various CPPs conventionally known in the related art. For example, so-called polyarginine (Rn) consisting of 3 or more or preferably 5 or more and 11 or less or preferably 9 or less arginine residues is suitable as a CPP used here. In addition, various known CPPs can be employed.

Since a CPP contains a plurality of basic amino acids, it has high polarity (that is, high basicity). Therefore, solubility in a polar solvent (for example, PBS and physiological saline) with a CTLA4-B7 protein binding inhibitory peptide sequence can be enhanced.

Although not particularly limited, suitable examples of amino acid sequences functioning as CPPs are shown in SEQ ID NOS: 16 to 32. Specifically, the suitable examples thereof are as follows.

An amino acid sequence of SEQ ID NO: 16 corresponds to a nucleolar localization signal (NoLS) consisting of 14 amino acid residues in total derived from a basic fibroblast growth factor FGF2.

An amino acid sequence of SEQ ID NO: 17 corresponds to an NoLS consisting of 19 amino acid residues in total derived from one kind of nucleolar protein (ApLLP).

An amino acid sequence of SEQ ID NO: 18 corresponds to an NoLS consisting of 16 amino acid residues in total derived from a protein (γ(1)34.5) of herpes simplex virus type 1 (HSV-1).

An amino acid sequence of SEQ ID NO: 19 corresponds to an NoLS consisting of 19 amino acid residues in total derived from p40 protein of human I-mfa domain-containing protein (HIC).

An amino acid sequence of SEQ ID NO: 20 corresponds to an NoLS consisting of 16 amino acid residues in total derived from MEQ protein of Marek's disease virus (MDV).

An amino acid sequence of SEQ ID NO: 21 corresponds to an NoLS consisting of 17 amino acid residues in total derived from Survivin-delta Ex3 which is a protein that suppresses apoptosis.

An amino acid sequence of SEQ ID NO: 22 corresponds to an NoLS consisting of 7 amino acid residues in total derived from Angiogenin which is a vascular growth factor.

An amino acid sequence of SEQ ID NO: 23 corresponds to an NoLS consisting of 8 amino acid residues in total derived from MDM2 which is a nuclear phosphoprotein forming a complex with p53 tumor inhibitory protein.

An amino acid sequence of SEQ ID NO: 24 corresponds to an NoLS consisting of 9 amino acid residues in total derived from betanodavirus protein GGNNVa.

An amino acid sequence of SEQ ID NO: 25 corresponds to an NoLS consisting of 7 amino acid residues in total derived from NF-κB-inducing kinase (NIK).

An amino acid sequence of SEQ ID NO: 26 corresponds to an NoLS consisting of 15 amino acid residues in total derived from nuclear VCP-like protein.

An amino acid sequence of SEQ ID NO: 27 corresponds to an NoLS consisting of 18 amino acid residues in total derived from nucleolar protein p120.

An amino acid sequence of SEQ ID NO: 28 corresponds to an NoLS consisting of 14 amino acid residues in total derived from ORF57 protein of herpes virus saimiri (HVS).

An amino acid sequence of SEQ ID NO: 29 corresponds to an NoLS consisting of 13 amino acid residues in total from the 491st amino acid residue to the 503rd amino acid residue of LIM kinase 2 existing in human endothelial cells, which is one kind of protein kinase involved in intracellular signal transduction.

An amino acid sequence of SEQ ID NO: 30 corresponds to an NoLS consisting of 8 amino acid residues in total contained in nucleocapsid protein (N protein) of avian infectious bronchitis virus (IBV).

An amino acid sequence of SEQ ID NO: 31 corresponds to a membrane-permeable motif consisting of 9 amino acid sequences in total derived from a protein transduction domain contained in TAT of human immunodeficiency virus (HIV).

An amino acid sequence of SEQ ID NO: 32 corresponds to a membrane-permeable motif consisting of 11 amino acid sequences in total of a protein transduction domain (PTD4) obtained by modifying above-described TAT.

An amino acid sequence represented by SEQ ID NO: 33 corresponds to a membrane-permeable motif consisting of 18 amino acid sequences in total derived from Antennapedia ANT which is a mutant of *Drosophila*.

Among these, amino acid sequences related to an NoLS and TAT (or modified amino acid sequences thereof) are particularly preferable. For example, an NoLS-related CPP sequence as shown in SEQ ID NO: 29 or 30 or TAT- or ANT-related CPP sequences of SEQ ID NO: 32 or 33 can be preferably used to construct the synthetic peptide disclosed herein.

By providing the above-described CPP-related sequence as an auxiliary peptide sequence, the CTLA4-B7 protein binding inhibitory peptide sequence can be easily dissolved and dispersed in the above-described predetermined solvent. In addition, for example, when the CTLA4-B7 protein binding inhibitory peptide sequence is supplied to cells (cultured cells or cultured tissue) or the like, the peptide sequence may easily permeate through a cell membrane of a target cell. For example, in a case where the synthetic peptide disclosed herein has a CPP-related sequence, an operation of approaching a target cell from outside becomes easier. Alternatively, the synthetic peptide can be localized in a cell membrane to more effectively suppress the binding of CTLA4 to B7 proteins.

In a case where the synthetic peptide disclosed herein has both the CTLA4-B7 protein binding inhibitory peptide sequence and an auxiliary peptide sequence, the auxiliary peptide sequence may be disposed on the N-terminal side or the C-terminal side relative to the CTLA4-B7 protein binding inhibitory peptide sequence. For example, the auxiliary peptide sequence is preferably disposed adjacent to the N-terminal side or the C-terminal side of the CTLA4-B7 protein binding inhibitory peptide sequence.

Specifically, amino acid residues not included in both sequence portions are preferably not present between the CTLA4-B7 protein binding inhibitory peptide sequence and the auxiliary peptide sequence. Alternatively, even if a linker is present, the number of amino acid residues functioning as a linker connecting the above-described two sequences is preferably 10 or less (and more preferably 5 or less, for example, 1 or 2 amino acid residues).

In the synthetic peptide disclosed herein, the total number of amino acid residues constituting a peptide chain is suitably 100 or less, preferably 80 or less, and more preferably 70 or less (for example, a peptide chain with about 40 to 60 amino acid residues, or a peptide chain with 40 or less amino acid resides is preferable). It is easy to chemically synthesize such a peptide having a short chain length, and therefore, it is possible to easily provide a synthetic peptide. Although not particularly limited, a linear or helical peptide is preferable from the viewpoint of being less likely to become an immunogen (antigen). A peptide having such a shape is unlikely to form epitopes.

The proportion of the CTLA4-B7 protein binding inhibitory peptide sequence in all the amino acid sequences of a synthesized peptide is not particularly limited as long as the CTLA4-B7 protein binding inhibitory properties are not lost. However, it is desirable that the proportion be roughly 35% by number or more, 40% by number or more, 45% by number or more, 50% by number or more, 55% by number or more, or 60% by number or more.

The ratio of the CTLA4-B7 protein binding inhibitory peptide sequence and the auxiliary peptide sequence to all the amino acid sequences of a synthesized peptide is not particularly limited as long as the CTLA4-B7 protein binding inhibitory properties are not lost. However, it is desirable that the ratio be roughly 60% by number or more, 70% by number or more, 80% by number or more, or 90% by number or more.

Although all amino acid residues are preferably L-amino acids, some or all of amino acid residues may be substituted with D-amino acids as long as the CTLA4-B7 protein binding inhibitory properties are not lost.

The synthetic peptide disclosed herein preferably has at least one amino acid residue amidated. Structural stability (for example, protease resistance) of a synthetic peptide can be improved by amidation of a carboxyl group of an amino acid residue (typically the C-terminal amino acid residue of a peptide chain). For example, when the C-terminus of a synthetic peptide is composed of a CTLA4-B7 protein binding inhibitory peptide sequence portion, the C-terminal amino acid residue of the sequence portion is preferably amidated. Meanwhile, for example, when a synthetic peptide contains an auxiliary peptide sequence and the C-terminus of the synthetic peptide is composed of the auxiliary peptide sequence portion, the C-terminal amino acid residue of the sequence portion is preferably amidated. In another preferred aspect, stability of a synthetic peptide having amino acid sequences of SEQ ID NOs: 34 to 36 can be improved by amidation of the C-terminal amino acid residue of the synthetic peptide, for example.

The synthetic peptide disclosed herein can be easily produced according to a usual chemical synthesis method. For example, either a solid-phase synthesis method or a liquid-phase synthesis method conventionally known in the related art may be employed. A solid-phase synthesis method in which a t-butyloxycarbonyl (Boc) group or a 9-fluorenylmethoxycarbonyl (Fmoc) group is applied as a protecting group for an amino group is suitable.

The synthetic peptide disclosed herein can be obtained by synthesizing a peptide chain having a desired amino acid sequence and a modified (C-terminal amidation or the like) portion through a solid-phase synthesis method using a commercially available peptide synthesizer.

Alternatively, a synthetic peptide can be produced through biosynthesis based on a genetic engineering technique. That is, a polynucleotide (typically DNA) of a nucleotide sequence (containing an ATG start codon) encoding a desired amino acid sequence of a synthetic peptide is synthesized. A recombinant vector having an expression gene construct consisting of the synthesized polynucleotide (DNA) and various regulatory elements (including a promoter, a ribosome binding site, a terminator, an enhancer, and various cis-elements controlling an expression level) for expressing the amino acid sequence in host cells is constructed depending on the host cells.

This recombinant vector is introduced into predetermined host cells (for example, yeast, insect cells, or plant cells) through an ordinary technique to culture the host cells, or tissue or an individual containing the cells under predetermined conditions. As a result, a target peptide can be expressed and produced in the cells. Then, the peptide can be isolated from the host cells (or from a culture medium in a case of being secreted therein), and refolding or purification can be performed as necessary to obtain a target synthetic peptide.

Since a method which has conventionally been carried out in the related art may be employed as it is as the method for constructing a recombinant vector and the method for introducing a recombinant vector into host cells and such methods themselves do not particularly characterize the present invention, detailed explanation thereof will be omitted.

Alternatively, a target polypeptide can be synthesized in vitro by employing a so-called cell-free protein synthesis system by constructing template DNA for the cell-free protein synthesis system (that is, a synthetic gene fragment containing a nucleotide sequence that encodes an amino acid sequence of a synthetic peptide) and using various compounds (such as ATP, RNA polymerase, and amino acids) required for peptide synthesis. Regarding the cell-free protein synthesis system, a paper of Shimizu et al. (Shimizu, et al., Nature Biotechnology, 19, 751-755 (2001)) and a paper of Madin et al. (Madin et al., Proc. Natl. Acad. Sci., USA, 97(2), 559-564 (2000)) can be referred to, for example. Many private companies have already undertaken contract production of polypeptides based on the techniques described in these papers at the time of filing the present application, and cell-free protein synthesis kits are available commercially (for example, available from CellFree Sciences Co., Ltd. in Japan).

A nucleotide sequence encoding the synthetic peptide disclosed herein and/or a single-stranded or double-stranded polynucleotide containing a nucleotide sequence complementary to the nucleotide sequence encoding the synthetic peptide can be easily produced (synthesized) according to a method conventionally known in the related art. That is, a codon corresponding to each amino acid residue constituting a designed amino acid sequence is selected to easily determine and provide a nucleotide sequence corresponding to the amino acid sequence of the synthetic peptide. Once the nucleotide sequence is determined, a (single-stranded) polynucleotide corresponding to the desired nucleotide sequence can be easily obtained using a DNA synthesizer or the like. A target double-stranded DNA can be further obtained by using the obtained single-stranded DNA as a template and employing various enzymatic synthesis means (typically, PCR). In addition, the polynucleotide may be in a form of DNA or in a form of RNA (mRNA or the like). DNA can be provided as a double strand or a single strand. In the case where DNA is provided as a single strand, the strand may be a coding strand (sense strand) or non-coding strand (antisense strand) of a sequence complementary thereto.

The polynucleotide obtained in this manner can be used as a material for constructing a recombinant gene (expression cassette) for producing a synthetic peptide in various host cells or with a cell-free protein synthesis system as described above.

The synthetic peptide disclosed herein can be suitably used as an active component of a composition for applications of suppressing binding of CTLA4 to B7 proteins. Furthermore, the synthetic peptide may be in a form of a salt as long as the above-described binding inhibitory properties are not lost. For example, an acid addition salt of a synthetic peptide that can be obtained through an addition reaction of an ordinarily used inorganic acid or organic acid can be used according to a usual method. Accordingly, the "peptide" described in the present specification and claims includes such a salt form.

The composition disclosed herein may contain various pharmaceutically acceptable carriers depending on a usage form as long as the activity of the synthetic peptide as an active component is not lost. For example, carriers commonly used in peptide pharmaceuticals can be suitably applied as diluents, excipients, and the like.

Although the carriers may appropriately vary depending on the applications or forms of the composition disclosed herein, typical examples thereof include water, a physiological buffer solution, and various organic solvents. An aqueous alcohol (such as ethanol) solution at an appropriate concentration, glycerol, and non-drying oils such as olive oil can be used. Alternatively, a liposome may be used. In addition, examples of secondary components that can be contained in the composition include various fillers, extenders, binders, humectants, surfactants, pigments, and fragrances.

Examples of typical forms of compositions (medicines) include a liquid medicine, suspensions, emulsions, aerosols, foaming agents, granules, powdery agents, tablets, capsules, ointments and aqueous gel. In addition, the compositions may be freeze-dried products or granulated products for preparing a drug solution by dissolving the compositions in physiological saline or a suitable buffer solution (for example, PBS) immediately before use in order to use the compositions for injection or the like.

Since the process itself for preparing various forms of compositions (medicines) using the synthetic peptide (main component) and various carriers (secondary components) as materials may be based on a method conventionally known in the related art and such a production method itself does not characterize the present invention, detailed description thereof will be omitted. Examples of a detailed source of information on the formulations include Comprehensive Medicinal Chemistry, supervised by Corwin Hansch, published by Pergamon Press (1990). The entire contents of this publication are incorporated in the present specification by reference.

The CTLA4-B7 protein binding inhibitory properties of the composition (synthetic peptide) disclosed herein can be evaluated through, for example, the following method.

The method for evaluating the CTLA4-B7 protein binding inhibitory properties includes placing CTLA4 on the surface of a base material, supplying the composition (synthetic peptide) disclosed herein to CTLA4, supplying B7 proteins, and detecting B7 proteins bound to CTLA4.

In this method, CTLA4 is first placed on the surface of a base material. The placement means is not particularly limited, and various coating means and immobilization means can be used. For example, a solution, dispersion liquid, or the like of CTLA4 can be brought into contact with the surface of a base material for a predetermined period of time to place CTLA4 on the surface of the base material. The conditions are not particularly limited, but it is preferable that, for example, the surface of the base material be brought into contact with a solution (or a dispersion liquid) containing CTLA4 for a period of about overnight under the condition of a temperature of 4° C.

Although the base material is not particularly limited as long as CTLA4 can be placed on the surface thereof, a base material made of resin or glass can be used, for example. For example, commercially available microplates, dishes, microbeads, and the like can be suitably used. The surface of a base material may be modified as necessary to improve the occupancy rate (that is, an arrangement area, a coating rate, or an abundance) of CTLA4 on the surface of the base material, for example.

The degree to which CTLA4 is placed on the surface of a base material is not particularly limited.

Next, a suitable amount of the composition (synthetic peptide) disclosed herein is supplied to CTLA4 at least once. The amount and the number of times of supply per supply may vary depending on the kind of base material on which CTLA4 is placed, the abundance rate on the surface of a base material, the temperature conditions, and the like, and therefore are not particularly limited. For example, the final concentration of a synthetic peptide at the time of incubation with CTLA4 is roughly within a range of 0.1 µM to 100 µM and preferably within a range of 1 µM to 50 µM (for example, 2.5 µM to 25 µM).

Supply of B7 proteins to CTLA4 may be performed after the supply of the composition (synthetic peptide) disclosed herein to CTLA4 as described above, or simultaneously with the supply of the composition (synthetic peptide).

For example, in the case of supplying B7 proteins to CTLA4 after the supply of the composition (synthetic peptide) thereto, the B7 proteins are preferably supplied in the presence of the synthetic peptide.

For example, in the case of simultaneously supplying the synthetic peptide and B7 proteins to CTLA4, the synthetic peptide and the B7 proteins may be brought into contact with each other in advance for a predetermined period.

The amount and the number of times of supply of B7 proteins per supply may vary depending on the kind of base material on which CTLA4 is placed, the occupancy rate on the surface of a base material, the temperature conditions, and the like, and therefore are not particularly limited.

Methods for detecting B7 proteins bound to CTLA4 are not particularly limited, but typical examples thereof include detecting biotin-streptavidin binding and an immunological detection method. B7 proteins bound to CTLA4 are preferably detected based on biotin-streptavidin binding, for example. For example, biotin-labeled B7 proteins can be used, and fluorescence-labeled or enzyme-labeled (for example, horseradish-derived peroxidase-labeled or alkaline phosphatase-labeled) streptavidin can be suitably used.

Although not particularly limited, an example of the method for evaluating suppression of binding is shown in the following examples.

A method for suppressing binding of CTLA4 to B7 proteins in vivo or in vitro using the composition (synthetic peptide) disclosed herein is provided. This method includes supplying the composition (synthetic peptide) disclosed herein at least once to a system in which CTLA4 and B7 proteins coexist.

The above-described "system" in vivo includes, for example, various kinds of tissues, organs, blood, and lymph. The above-described "system" in vitro includes, for example, various kinds of cell aggregation, tissues, organs, blood, lymph, and cell lines removed from a living body.

The composition disclosed herein can be used in a method or dose according to its form and purpose similarly to conventional peptide preparations in the related art. For example, the composition can be administered as a liquid agent to a lesion part (typically, malignant tumor tissue) of a patient (that is, a living body) in a desired amount through intravenous, intramuscular, subcutaneous, intradermal, or intraperitoneal injection. Alternatively, the composition in a solid form such as a tablet, or a gel form or an aqueous jelly form such as an ointment, can be directly administered to a predetermined tissue (that is a lesion part such as an organ or tissue containing tumor cells). Alternatively, the composition in a solid form such as a tablet can be orally administered. In the case of oral administration, it is preferable to apply encapsulation or a protective (coating) material to suppress digestive enzyme decomposition in the digestive tract.

Alternatively, in co-culture of, for example, CTLA4-expressing cells and B7 protein-expressing cells cultured in vitro, a suitable amount of the composition (that is, a suitable amount of the synthetic peptide) disclosed herein may be supplied to a medium of the target cultured cell (or tissue or the like) at least once. The amount and the number of times of supply per supply may vary depending on the conditions such as the kinds of cell to be cultured, the cell density (cell density at the start of culture), the number of subcultures, culture conditions, and kinds of media, and therefore are not particularly limited. However, it is preferable that the composition be added thereto once, twice, or multiple times so that the concentration of synthetic peptide in a medium is roughly within a range of 0.5 µM to 100 µM and preferably within a range of 3 µM to 50 µM (for example, 6.25 µM to 25 µM).

Examples of the above-described CTLA4-expressing cells include T cells (including a case of cultured cell lines, a cell aggregation removed from a living body, or a tissue or an organ containing T cells) and CTLA4-expressing cells produced through conventionally known genetic manipulation (for example, transfection) of cultured cells in the related art. In addition, examples of the above-described B7 protein-expressing cells include antigen-presenting cells (including a case of cultured cell lines, a cell aggregation removed from a living body, or a tissue or an organ containing these cells) and B7 protein-expressing cells produced through conventionally known genetic manipulation (for example, transfection) of cultured cells in the related art.

Hereinafter, several examples of the present invention will be described, but the present invention is not intended to be limited to those shown in such examples.

Test Example 1: Peptide Synthesis

Six kinds of sample peptides shown in Table 1 were produced using a commercially available peptide synthesizer. Specifically, the samples are as follows.

Sample 1 is a synthetic peptide (SEQ ID NO: 34) including both an amino acid sequence constituting a signal peptide of human CTLA4 represented by SEQ ID NO: 8 as a CTLA4-SP-related sequence and an amino acid sequence (LIM kinase 2) shown in SEQ ID NO: 29 as an auxiliary amino acid sequence.

Sample 2 is a synthetic peptide (SEQ ID NO: 35) including both an amino acid sequence constituting a signal peptide of human TIM3 represented by SEQ ID NO: 1 as a TIM3-SP-related sequence and an amino acid sequence (LIM kinase 2) shown in SEQ ID NO: 29 as an auxiliary amino acid sequence.

Sample 3 is a synthetic peptide (SEQ ID NO: 36) including both an amino acid sequence constituting a signal peptide of human LAG5 represented by SEQ ID NO: 5 as an LAG5-SP-related sequence and an amino acid sequence (LIM kinase 2) shown in SEQ ID NO: 29 as an auxiliary amino acid sequence.

Sample 4 is an amino acid sequence (SEQ ID NO: 37) constituting a signal peptide of human PD-1.

Sample 5 is a synthetic peptide (SEQ ID NO: 38) having a tandem repeat sequence of an amino acid sequence constituting a signal peptide of human PD-1.

Sample 6 is a synthetic peptide (SEQ ID NO: 39) having the amino acid sequences (LIM kinase 2) shown in SEQ ID NO: 29 which are auxiliary amino acid sequences of the Samples 1 to 3.

TABLE 1

| Sample ID | Sequence | Number of amino acid residues | SEQ ID NOs: |
|---|---|---|---|
| Sample 1 | MACLGFQRHKAQLNLATRTWPCTLLFFL LFIPVFCKKRTLRKNDRKKR | 48 | 34 |
| Sample 2 | MFSHLPFDCVLLLLLLLLLTRSKKRTLRK NDRKKR | 34 | 35 |
| Sample 3 | MWEAQFLGLLFLQPLWVAPVKPLQPGAE KKRTLRKNDRKKR | 41 | 36 |
| Sample 4 | MQIPQAPWPVVWAVLQLGWR | 2 | 37 |
| Sample 5 | MQIPQAPWPVVWAVLQLGWRMQIPQAPW RPVVWAVLQLGW | 40 | 38 |
| Sample 6 | KKRTLRKNDR KKR | 13 | 39 |

The above-described sample peptides were synthesized by carrying out a solid-phase synthesis method (Fmoc method) using a commercially available peptide synthesizer according to the manual. Since the mode of use of the peptide synthesizer itself does not characterize the present invention, detailed description will be omitted. The synthetic peptides shown in Table 1 were peptides having the amino acid sequences shown in SEQ ID NOs: 34 to 39 in which a carboxyl group (—COOH) of the C-terminal amino acid residue was amidated (—CONH$_2$).

The synthesized sample peptides were dissolved in PBS to prepare stock solutions (with a concentration of 2.5 mM).

Test Example 2: Test for Evaluating Binding Inhibitory Properties Between CTLA4 and B7-1

The binding inhibitory properties between CTLA4 and B7-1 were evaluated for the 6 kinds of sample peptides synthesized in the above-described Test Example 1.

In this test, Test Examples 2-1 to 2-9 were set according to the kinds of sample peptide used and the peptide concentration as shown in Table 2 below. In addition, a peptide-free group was set as Test Example 2-10. The tests of the above-described 10 categories in total were carried out as follows. The numbers "1 to 10" shown in the "No." column of Table 2 represent "Test Examples 2-1 to 2-10" in Test Example 2. In addition, the number (n) of test wells in each of the above-described examples was set to 2.

TABLE 2

| No. | Peptide | Peptide concentration (µM) |
| --- | --- | --- |
| 1 | Sample 1 | 5 |
| 2 | | 10 |
| 3 | Sample 2 | 5 |
| 4 | | 10 |
| 5 | Sample 3 | 10 |
| 6 | Sample 4 | 10 |
| 7 | Sample 5 | 10 |
| 8 | Sample 6 | 5 |
| 9 | | 10 |
| 10 | No peptide added | — |

Test Example 2-1

In Test Example 2-1, the following kit currently available on the market was used. CTLA4 B7-1 (Biotinylated) inhibitor screening assay kit (manufactured by BPS Bioscience, BPS #72009)

The operation for this test example was based on "ASSAY PROTOCOL" described in the data sheet of the above-described kit. A brief procedure is shown below.

First, each well of a 96-well plate was coated with CTLA4. Specifically, a CTLA4 solution (2 µg/mL) was dispensed into each well of the 96-well plate, and the plate was incubated overnight at 4° C.

Subsequently, the CTLA4 solution was removed, and each well was washed.

Subsequently, blocking was performed. Specifically, a blocking buffer contained in the kit was dispensed into each well, and the plate was incubated for 1 hour at room temperature.

Subsequently, a solution of the Sample 1 was dispensed into each well, and the plate was incubated for 1 hour at room temperature.

Subsequently, a biotin-labeled B7-1 solution (1.25 ng/mL) was dispensed into each well of the 96-well plate, and the plate was incubated for 2 hours at room temperature.

After the above-described incubation, the peptide solution was removed, and each well was washed.

Thereafter, blocking was performed as described above.

After the above-described blocking, a Streptavidin-HRP solution (1,000-fold diluted solution) was dispensed into each well, and the plate was incubated for 45 minutes at room temperature.

After the above-described incubation, the Streptavidin-HRP solution was removed, and each well was washed.

Thereafter, blocking was performed for 10 minutes.

Subsequently, the blocking buffer was removed, a chemiluminescent reagent contained in the above-described kit was dispensed into each well, and the chemiluminescence intensity in each well was measured with a luminometer.

A value obtained by subtracting an average value of the chemiluminescence intensity in a blank well from an average value of the chemiluminescence intensity in each well was taken as a measurement value of Test Example 2-1.

Test Example 2-2

Test Example 2-2 was performed using the same materials and processes as those of Test Example 2-1 except that the peptide of the Sample 1 was used at the concentration shown in Table 2.

Test Example 2-3

Test Example 2-3 was performed using the same materials and processes as those of Test Example 2-1 except that the peptide of the Sample 2 was used at the concentration shown in Table 2 in place of the peptide of the Sample 1.

Test Example 2-4

Test Example 2-4 was performed using the same materials and processes as those of Test Example 2-1 except that the peptide of the Sample 2 was used at the concentration shown in Table 2 in place of the peptide of the Sample 1.

Test Example 2-5

Test Example 2-5 was performed using the same materials and processes as those of Test Example 2-1 except that the peptide of the Sample 3 was used at the concentration shown in Table 2 in place of the peptide of the Sample 1.

Test Example 2-6

Test Example 2-6 was performed using the same materials and processes as those of Test Example 2-1 except that the peptide of the Sample 4 was used at the concentration shown in Table 2 in place of the peptide of the Sample 1.

Test Example 2-7

Test Example 2-7 was performed using the same materials and processes as those of Test Example 2-1 except that the peptide of the Sample 5 was used at the concentration shown in Table 2 in place of the peptide of the Sample 1.

Test Example 2-8

Test Example 2-8 was performed using the same materials and processes as those of Test Example 2-1 except that the peptide of the Sample 6 was used at the concentration shown in Table 2 in place of the peptide of the Sample 1.

Test Example 2-9

Test Example 2-9 was performed using the same materials and processes as those of Test Example 2-1 except that the peptide of the Sample 6 was used at the concentration shown in Table 2 in place of the peptide of the Sample 1.

Test Example 2-10

Test Example 2-10 was performed using the same materials and processes as those of Test Example 2-1 except that no sample peptide was added.

Measurement values of the obtained Test Examples 2-1 to 2-10 described above are shown in FIG. 1.

Figure 1:
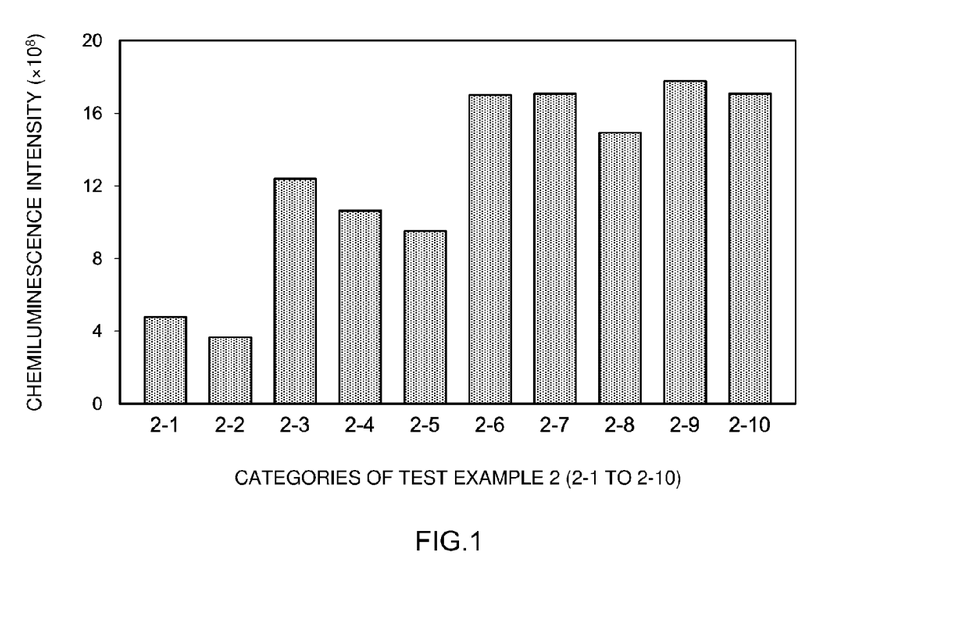

As shown in FIG. 1, binding of CTLA4 to B7-1 was observed in Test Example 2-10 in which no sample peptide was added. On the other hand, it was found that the binding of CTLA4 to B7-1 was significantly suppressed by adding any of the Samples 1 to 3 at all the peptide concentrations (5 μM, 10 μM) used at this time (Test Examples 2-1 to 2-5). On the other hand, no action of suppressing the binding of CTLA4 to B7-1 was observed in any of the Samples 4 and 5 (Test Examples 2-6 and 2-7). Furthermore, the bonding of CTLA4 to B7-1 was not suppressed in the Sample 6 which was a synthetic peptide having an amino acid sequence of LIMK2 as an auxiliary sequence of each of the Samples 1 to 5 (Test Examples 2-8 and 2-9).

From the above-described results, it was found that the CTLA4-SP-related sequence, the TIM3-SP-related sequence, and the LAGS-SP-related sequence respectively represented by the Samples 1 to 3 had excellent CTLA4-B7-1 binding inhibitory properties.

Test Example 3: Test for Evaluating Binding Inhibitory Properties Between CTLA4 and B7-2

The binding inhibitory properties between CTLA4 and B7-2 were evaluated for the 6 kinds of sample peptides synthesized in the above-described Test Example 1.

In this test, Test Examples 3-1 to 3-9 were set according to the kind of sample peptide used and the peptide concentration as shown in Table 2 mentioned above. In addition, a peptide-free group was set as Test Example 3-10. The tests of the above-described 10 categories in total were carried out as follows. The numbers "1 to 10" shown in the "No." column of Table 2 represent "Test Examples 3-1 to 3-10" in Test Example 3. In addition, the number (n) of test wells in each of the above-described examples was set to 2.

Test Example 3-1

In Test Example 3-1, the following kit currently available on the market was used. CTLA4 B7-2 (Biotinylated) inhibitor screening assay kit (BPS #79658)

The operation for this test example was based on "ASSAY PROTOCOL" described in the data sheet of the above-described kit.

Test Example 3-1 was performed using the same materials and processes as those of Test Example 2-1 except that the above-described kit was used.

Test Example 3-2

Test Example 3-2 was performed using the same materials and processes as those of Test Example 3-1 except that the peptide of the Sample 1 was used at the concentration shown in Table 2.

Test Example 3-3

Test Example 3-3 was performed using the same materials and processes as those of Test Example 3-1 except that the peptide of the Sample 2 was used at the concentration shown in Table 2 in place of the peptide of the Sample 1.

Test Example 3-4

Test Example 3-4 was performed using the same materials and processes as those of Test Example 3-1 except that the peptide of the Sample 2 was used at the concentration shown in Table 2 in place of the peptide of the Sample 1.

Test Example 3-5

Test Example 3-5 was performed using the same materials and processes as those of Test Example 3-1 except that the peptide of the Sample 3 was used at the concentration shown in Table 2 in place of the peptide of the Sample 1.

Test Example 3-6

Test Example 3-6 was performed using the same materials and processes as those of Test Example 3-1 except that the peptide of the Sample 4 was used at the concentration shown in Table 2 in place of the peptide of the Sample 1.

Test Example 3-7

Test Example 3-7 was performed using the same materials and processes as those of Test Example 3-1 except that the peptide of the Sample 5 was used at the concentration shown in Table 2 in place of the peptide of the Sample 1.

Test Example 3-8

Test Example 3-8 was performed using the same materials and processes as those of Test Example 3-1 except that the peptide of the Sample 6 was used at the concentration shown in Table 2 in place of the peptide of the Sample 1.

Test Example 3-9

Test Example 3-9 was performed using the same materials and processes as those of Test Example 3-1 except that the peptide of the Sample 6 was used at the concentration shown in Table 2 in place of the peptide of the Sample 1.

Test Example 3-10

Test Example 3-10 was performed using the same materials and processes as those of Test Example 3-1 except that no sample peptide was added.

Measurement values of the obtained Test Examples 3-1 to 3-10 described above are shown in FIG. 2.

Figure 2:
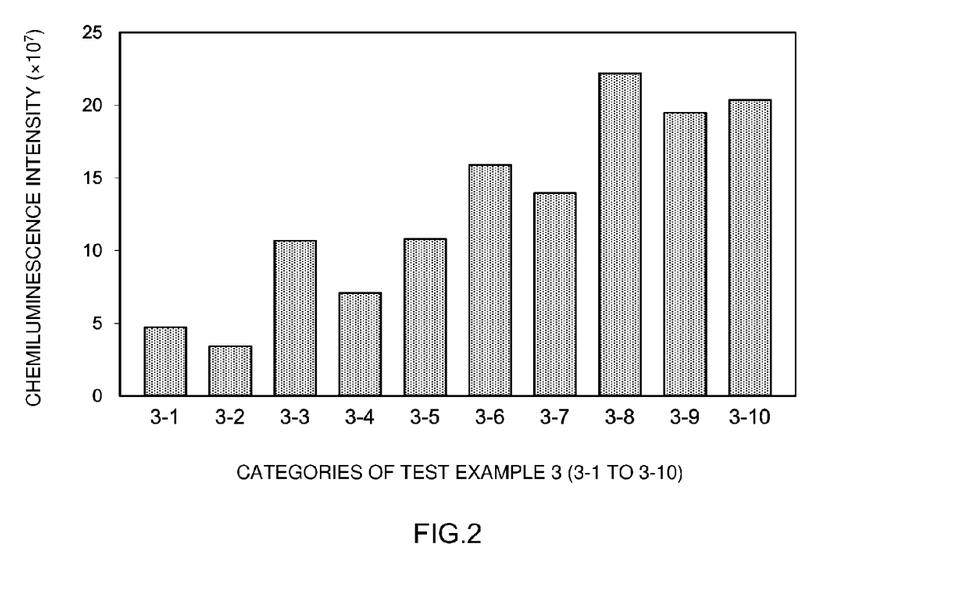

As shown in FIG. 2, binding of CTLA4 to B7-2 was observed in Test Example 3-10 in which no sample peptide was added. It was found that the binding of CTLA4 to B7-2 was suppressed by adding any of the Samples 1 to 5 at all the peptide concentrations (5 μM, 10 μM) used at this time (Test Examples 3-1 to 3-7). It was found that the binding of CTLA4 to B7-2 was more strongly suppressed by adding any of the Samples 1 to 3. The bonding of CTLA4 to B7-2 was not suppressed in the Sample 6 which was a synthetic peptide having an amino acid sequence of LIMK2 as an auxiliary sequence of each of the Samples 1 to 5 (Test Examples 3-8 and 3-9). From the above-described results, it was found that the CTLA4-SP-related sequence, the TIM3-SP-related sequence, and the LAGS-SP-related sequence respectively represented by the Samples 1 to 3 had particularly excellent CTLA4-B7-2 binding inhibitory properties.

As described above, it was found that the CTLA4-SP-related sequence, the LAG3-SP-related sequence, and the TIM3-SP-related sequence had excellent CTLA4-B7 protein binding inhibitory properties.

As described above, according to the synthetic peptide and the composition disclosed herein, it is possible to suppress binding of CTLA4 to at least one of B7-1 and B7-2.

In this manner, the synthetic peptide and the composition provided by the present invention have the same activity as an anti-CTLA4 antibody. For this reason, it is possible to provide pharmaceutical compositions having, for example, the same activity as antibody pharmaceuticals containing the above-described antibody using the synthetic peptide and the composition disclosed herein. The techniques disclosed herein can be suitably implemented in the medical industries, medical research, and the like.

The invention claimed is:

1. A synthetic peptide which is artificially synthesized and suppresses binding of cytotoxic T lymphocyte antigen 4 (CTLA4) to at least one of B7 proteins B7-1 and B7-2, the peptide comprising the amino acid sequence shown in any one of SEQ ID NOs: 35 and 36, wherein the total number of amino acid residues is 100 or less.

2. A composition for suppressing binding of cytotoxic T lymphocyte antigen 4 (CTLA4) to at least one of B7 proteins B7-1 and B7-2, the composition comprising:

at least one pharmaceutically acceptable carrier; and a synthetic peptide comprising an amino acid sequence shown in any one of SEQ ID NOs: 35 and 36, wherein the total number of amino acid residues in the synthetic peptide is 100 or less.

3. A method for suppressing binding of CTLA4 to at least one of B7 proteins B7-1 and B7-2, in vitro or in vivo, the method comprising: contacting blood, lymph, tissues, organs, or cell lines removed from a living body with the synthetic peptide according to claim 1, wherein the blood, lymph, tissues, organs, or cell lines express CTLA4 and B7-1 or B7-2.

* * * * *